(12) United States Patent
Mukherjee et al.

(10) Patent No.: US 6,440,432 B1
(45) Date of Patent: Aug. 27, 2002

(54) SKIN COSMETIC COMPOSITIONS CONTAINING DEXTRAN OR MALTODEXTRIN AND A WEAK CARBOXYLIC ACID

(75) Inventors: Surajit Mukherjee, Ridgewood; Donald Rick, Dumont; Stephan Samuel Habif, Demarest; Ronni Lynn Weinkauf, River Edge, all of NJ (US)

(73) Assignee: Unilever Home & Personal Care USA, a division of Conopco, Inc., Greewich, CT (US)

( * ) Notice: Subject to any disclaimer, the term of this patent is extended or adjusted under 35 U.S.C. 154(b) by 0 days.

(21) Appl. No.: 09/490,270

(22) Filed: Jan. 24, 2000

Related U.S. Application Data

(60) Provisional application No. 60/124,959, filed on Mar. 18, 1999.

(51) Int. Cl.⁷ .................... A61K 7/00; A61K 31/715; A01N 43/04
(52) U.S. Cl. .................... 424/401; 514/59; 514/60; 514/844; 514/938
(58) Field of Search .................... 424/401; 514/59, 514/60, 844, 938

(56) References Cited

U.S. PATENT DOCUMENTS

| | | | | |
|---|---|---|---|---|
| 4,105,783 A | | 8/1978 | Yu et al. ............ | 424/283 |
| 5,215,759 A | * | 6/1993 | Mausner ............ | 424/489 |
| 5,391,373 A | * | 2/1995 | Mausner ............ | 424/401 |
| 5,407,677 A | * | 4/1995 | Tominaga et al. ..... | 424/401 |
| 5,411,734 A | | 5/1995 | Vargas et al. ........ | 424/401 |
| 5,618,850 A | | 4/1997 | Coury et al. ........ | 514/772.2 |
| 5,698,187 A | * | 12/1997 | Naggiar ............ | 424/73 |
| 5,716,625 A | | 2/1998 | Hahn et al. ......... | 424/401 |
| 5,952,373 A | * | 9/1999 | Lanzendorfer et al. .. | 514/456 |
| 6,046,178 A | * | 4/2000 | Silvetti, Sr. ........ | 514/60 |

FOREIGN PATENT DOCUMENTS

| | | |
|---|---|---|
| EP | 0 691 126 a 1 | 6/1995 |
| EP | 0 937 454 A 2 | 2/1999 |
| JP | 02167212 A * | 6/1990 |
| JP | 04295412 * | 10/1992 |
| JP | 07196479 A * | 8/1995 |
| WO | 95/17160 | 6/1995 |
| WO | 98/56345 | 12/1998 |
| WO | 00/32157 | 6/2000 |

OTHER PUBLICATIONS

International Search Report, Oct. 2000.
Larex (May 1998), Lara Care A200, Technical Bulletin–Exfoliation.

\* cited by examiner

*Primary Examiner*—Jose' G. Dees
*Assistant Examiner*—Marina Lamm
(74) *Attorney, Agent, or Firm*—Ellen Plotkin

(57) ABSTRACT

Cosmetic skin compositions containing a dextran or maltodextrin and a weak carboxylic acid. Dextran enhances the anti-aging activity of the weak acids and reduces skin irritation that is sometimes caused by the weak acid active.

10 Claims, No Drawings

SKIN COSMETIC COMPOSITIONS CONTAINING DEXTRAN OR MALTODEXTRIN AND A WEAK CARBOXYLIC ACID

This application claims the benefit of U.S. Provisional Application No. 60/124,959, filed Mar. 18, 1999.

FIELD OF THE INVENTION

Cosmetic compositions for human skin containing a dextran or maltodextrin and a weak carboxylic acid.

BACKGROUND OF THE INVENTION

Cosmetic products which improve the appearance of skin are increasingly popular with consumers. Frequently, consumers seek to alleviate or delay the signs of aged or photoaged skin, such as fine lines and wrinkles, dry and sagging skin. Consumers also seek other benefits in addition to anti-aging.

Some ingredients used in topical products are potentially irritating, especially to people with "sensitive skin." Such irritation is commonly perceived as sting or burning.

As an example, hydroxy acids and several other weak carboxylic acids have been proven to deliver cosmetic benefits, such as improvement in the appearance of photodamaged or naturally aged skin, skin lightening, treatment of age spots, etc. Unfortunately, their use at high concentrations may occasionally be associated with skin irritation, e.g. skin redness and stinging sensation upon application. For aesthetic reasons, these actives are most often delivered as oil-in-water emulsions. Practically, the final composition pH should be higher than 3 in order to prevent deleterious effects to skin tissues and unacceptable levels of irritation. Water soluble weak acids when delivered from an oil-in-water emulsion at acidic pH often induce high levels of sting. The sting occurs immediately after application, reaches a maximum intensity usually by 5–8 minutes after application and then begins to reduce in intensity.

The irritation can be ameliorated by lowering the amount of an active ingredient in the composition or by reducing the active's penetration through the skin. A serious drawback of both approaches is that the efficacy is impaired. The weak acid related irritation can be reduced by raising the composition's pH but this method yields reduced efficacy due to a decreased acid penetration through the skin. It is desirable to reduce or eliminate the irritation potential of weak acids while maintaining their efficacy.

The need exists, therefore, for a composition and method that prevents or reduces the skin irritation.

Coury et al. (U.S. Pat. No. 5,618,850) discloses cosmetic compositions containing polyhydroxy acids conjugated to the dextran polymer. EP 691126 (Beiersdorf) discloses cosmetic compositions with low stinging potential for treatment of sensitive skin. The compositions contain pigment to sequester AHA. A serious shortcoming of the Coury and Beirsdorf disclosures is that conjugation or sequestration significantly reduces delivery of the active and its efficacy. Most actives in current use have molecular weight less than 1000 Dalton. The penetration of actives through the skin decreases strongly with its molecular weight (Ref: Transdermal Delivery of Drugs; Volume III, P 7–8. Agis F. Kydonieus and Bret Berner (ed) CRC Press, Inc Boca Raton, Fla., 1987). Polymers have high (>>1000 Dalton) molecular weight. Conjugation of actives with the polymer Dextran will make it a high molecular weight molecule and hence will significantly lower penetration. Sequestration of the weak acid will reduce the amount of acid that would be available for delivery.

Another approach to lower the sting is to formulate the acid with a strong alkali metal base. Yu et al. (U.S. Pat. No. 4,105,783) suggested the use of ammonium hydroxide or an organic base. Unfortunately, this method raises the pH of the composition and reduces the ability of the weak acid to penetrate the skin, thus lowering its efficacy (see Sah et al. in *J. Cosmet. Sci.* 49, 257–273, 1998).

A clear need exists for a cosmetic composition with a weak acid that reduces sting but does not reduce dermal delivery.

Publication from LAREX (Mar. 23, 1998) discloses the use of a polysaccharide (arabinogalactan) to increase the exfoliation performance of a skin care lotion containing alpha hydroxy acid by 80% and to do so without increased irritation. The present invention, however, aims to decrease irritation, rather than merely not increasing it. It has been found, as part of the present invention, that other polysaccharides, dextran and maltodextrin, decrease irritation associated with the use of weak carboxylic acids, whereas arabinogalactan does not have this effect. Additionally, it has been found that dextran, unlike arabinogalactan, enhances the anti-aging efficacy of hydroxy acids.

SUMMARY OF THE INVENTION

The present invention includes a skin cosmetic composition comprising:
 (i) from about 0.5 to about 20 wt. % of a dextran or maltodextrin;
 (ii) from about 0.01 to about 20 wt. % of a weak carboxylic acid having pKa of above about 2; and
 (iii) a cosmetically acceptable vehicle.

The invention also includes cosmetic methods of stimulating collagen synthesis by fibroblasts and keratinocyte differentiation in the skin, by applying to the skin the inventive composition.

The invention also includes a cosmetic method of treating or delaying aged, chronoaged, photoaged, dry, lined or wrinkled skin, increasing stratum corneum firmness and flexibility, improving skin tone, and generally increasing the quality of skin by applying to the skin the inventive composition.

The invention further provides a method for reducing skin irritation caused by the topical application of a composition containing a weak carboxylic acid, the method comprising topically applying a dextran or maltodextrin in a cosmetically acceptable vehicle. Thus, according to this inventive method, the dextran or maltodextrin may be co-present with a weak acid in the same composition, or it may be applied from a separate composition.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the oil-in-water emulsion, unless otherwise specified.

The term "skin" as used herein includes the skin on the face, neck, chest, back, arms, armpits, hands and scalp.

The terms "irritation," "sting," and "burn," "inflammation,", and "redness" as used herein are synonymous and are used interchangeably.

The molecular weight is expressed in Dalton (D). The numerical terms followed by letters "KD" denote molecular weight of a compound, to be read as the numerical term ×1,000 e.g. 10 KD means molecular weight of 10,000 D).

Dextran

Both dextran and maltodextrin are glucose homopolymers.

Dextran is a beta-1,6-glucan with several glucose side chains, bound primarily to the main chain of the macromolecule through 1,3-linkages but, in part also by 1,4- and 1,2-linkages. On the average, 95% of the glucose residues are present in the main chain. It is produced by certain bacteria from a nutrient medium containing saccharose. The molecular weight of dextrans generally ranges from 5 KD to 2,000 KD, preferably from 5 KD to 1,000 KD, to maintain anti-iiritation efficacy, yet to minimize increase in formulation viscosity.

Maltodextrin

Maltodextrins $(C_6H_{10}O_5)_n \cdot H_2O$ (CAS Reg. No. 9050-36-6 are non-sweet nutritive saccharide polymers that consist of D-glucose units linked primarily by alpha-1,4-bonds, having a DE (Dextrose Equivalence) less than 20. They are prepared as a white powder or concentrated solution by partial hydrolysis of corn starch with safe and suitable acids and/or enzymes. The suitable source of maltodextrin is Maltrin® from Grain Processing Corp. Matrin® contains maltodextrin and corn syrup solids.

The amount of dextran or maltodextrin in the inventive composition ranges from 0.5 to 20%, preferably from 1 to 15%, most preferably from 1 to 10%, by weight of the composition.

Weak Carboxylic Acid

A weak carboxylic acid suitable for use in the inventive compositions is an acid with dissociation constant, pKa, of above about 2. Preferably, the pKa is above about 3, most preferably in the range of from about 3 to about 5.

The Concept of pKa

An acid is a species having a tendency to lose a proton, while a base is a species having a tendency to accept a proton. Hence for every acid, HA, there is a conjugate base A:

$$HA \rightleftharpoons H^+ + A^-$$

Thus, lactic acid-lactate ion is an example of a conjugate acid-base pair.

Acids so defined can only manifest their properties by reacting with bases. In aqueous solutions, acids react with water, the latter acting as a base $$HA + H_2O \rightleftharpoons H_3O^+ + A^-$$

Quantitatively, the acid strength of HA, relative to the base strength of water is given by the equilibrium constant expression by the equation $$K = [H_3O^+][A^-]/[H_2O][HA]$$

where parentheses denote molar concentrations.

As almost all measurements are made in dilute aqueous solution, the concentration of water remains essentially constant and its activity can be taken as unity. Letting $H^+$ represent the solvated proton, we have $$K_a = [H^+][A^-]/[HA],$$

where $K_a$ is the acidic dissociation (or ionization) constant. This equation can be written in the form $$pK_a = pH + \log [HA]/[A^-]$$

where $pK_a$ is the negative logarithm of $K_c$, and is equal to the pH at which the concentrations of HA and $A^-$ are equal.

$pK_a$ for alpha hydroxy acids are generally between 2–4, for monocarboxylic acids between 3–5, for alpha amino acids between 2–3; for salicylic acid it is 3.0.

The $pK_c$ of a weak water-soluble acid is obtained by titrating it with a strong base such as sodium hydroxide (NaOH). The intercept at the midpoint of the titration, ie. the point at which 0.5 molar equivalents of base have been added, is numerically equal to the pKa of the acid.

A procedure for determining pKa for a known weak acid is as follows:

Materials

Sample of pure acid for which pKa is to be determined; $CO_2$-free deionized distilled water (prepared by boiling deionized distilled water for 5 minutes); Commercial 0.1N NaOH volumetric standard, certified to 0.1005–0.0995 N, eg. Fisher Scientific SS276; 100-ml calibrated glass burette; 125-ml Erlenmeyer flask pH meter, eg. Corning Model 140 with standard combination electrode for pH; pH buffers, pH 4.00, 7.00, and 10.00, certified to ±0.01 pH unit at 25, eg. Fisher Scientific SB101, SB107, and SB115 magnetic stirrer

Method

Be sure all glassware and equipment is clean. Acid-wash if necessary. Prepare at least 50 ml of a 0.1 Normal solution of the acid for which the pKa is to be determined in $CO_2$-free distilled water. Avoid introducing $CO_2$ to the solution by avoiding excessive shaking. Cap the final solution until use.Calibrate the pH meter using three buffers, pH 7.00, 3.00, and 10.00, according to pH meter manufacturer's instructions. Rinse electrode with distilled water between samples. Fill burette with 0.1 N NaOH standard solution. Add 50.0 ml of 0.1 N acid solution to 125-ml Erienmeyer. Add stir bar to Erlenmeyer.

Insert pH electrode into acid solution. Position and secure electrode so that it does not interfere with stir bar. Record initial pH. Begin gentle stirring such that pH reading is not affected. Position burette over flask to allow incremental addition of 0.1 N standard NaOH to 0.1 N acid solution. Verify initial pH and begin incremental addition of base. Record the volumes of base added and resulting pH readings. Aim to record pH changes of 0.2 to 0.3 units or volume increases of about 5ml, whichever comes first. Continue incremental additions until at least 60 ml of base have been added and the steep change in pH levels off.

Plot the data with the volume of base as the x-axis and pH as the y-axis. Plot the points observed and draw a smooth line through them. Determine the volume of base added to obtain the equivalence point, i.e. the volume at which one normal- equivalent of base has been added and the acid has been completely neutralized: When the steep portion of the curve is vertical, the equivalence point volume corresponds to the volume of base at the vertical portion of the curve. If the steep portion of the curve is not vertical, the equivalence point can be obtained by locating the volumes of the base at the two end points that bracket the steep change in pH. The mean of the two volumes is the equivalence point.

To determine the pKa, first locate the midpoint of the titration by halving (i.e. ÷2) the volume of base at equivalence point. The midpoint of the titration is the point at which 0.5 normal-equivalents of base have been added, and the acid has been one-half (50%) neutralized. The pH corresponding to the midpoint of the titration is the $pK_a$ of the acid. This is the pH at which 50% of the acid has been neutralized, that is, and the molecule exists 50% in the non-ionized form and 50% as the anion.

Examples of suitable weak carboxylic acids include but are not limited to: alpha- or beta-hydroxyacids, dicarboxylic acids, tricarboxylic acids, ascorbic acid, oxamic acid and mixtures thereof. Preferred carboxylic acids, due to their anti-aging afficacy, are:

| ACID | pKa |
|---|---|
| glycolic | 3.8 |
| lactic | 3.8 |
| malic | 3.4 |
| beta-hydroxybutyric | 4.7 |
| acetic | 4.75 |
| succinic | 4.2 |
| citric | 3.1 |
| ascorbic | 4.1 |
| salicylic | 3.0 |
| oxamic | 2.4 | and mixtures thereof.

The amount of weak acid in the inventive composition ranges from 0.01 to 20%, preferably from 1 to 15% and most preferably from 2 to 12%, by weight of the composition. At concentrations below 2% of the acid, there is minimal stinging and the anti-aging efficacy does not increase significantly above 12%.

It is to be understood that depending on the pH of the composition, the acid may be present as a salt, e.g. ammonium or potassium or sodium salt.

Although the inventive compositions may have any pH in the general range of 2.5 to 10, the inventive compositions are particularly useful when they are at an acidic pH, preferably 3–6 and most preferably at a pH of 3–5, because such compositions, although efficacious, are particularly irritating.

The compositions according to the invention comprise a cosmetically acceptable vehicle to act as a diluant, dispersant or carrier for weak carboxylic acid and dextran or maltodextrin, so as to facilitate their distribution when the composition is applied to the skin.

The vehicle may be aqueous or an emulsion. Water when present will be in amounts which may range from 5 to 99%, preferably from 40 to 90%, optimally between 50 and 85% by weight.

According to the present invention, the vehicle is preferably at least 50 wt. % water, by weight of the vehicle. The inventive compositions are preferably oil-water emulsions, in order to improve dermal delivery of hydroxy acids (See Sah et al. in *J. Cosmet. Sci.* 49, 257–273, 1998). Such improved delivery is frequently accompanied by increased irritation/sting, making the use of dextran in such emulsions particularly critical. In the preferred oil-in-water emulsions according to the present invention, water comprises at least 50 wt. % of the inventive emulsion, most preferably from 50 to 85 wt. %, by weight of the composition.

Besides water, relatively volatile solvents may also serve as carriers within compositions of the present invention. Most preferred are monohydric $C_1$–$C_3$ alkanols. These include ethyl alcohol, methyl alcohol and isopropyl alcohol.

The amount of monohydric alkanol may range from 1 to 70%, preferably from 10 to 50%, optimally between 15 and 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3- butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively, the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di- $C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C20$ acyl isethionates, acyl glutamates, $C_8$–$C_{20}$ alkyl ether phosphates and combinations thereof.

Various types of additional active ingredients may be present in cosmetic compositions of the present invention. Actives are defined as skin benefit agents other than emollients and other than ingredients that merely improve the physical characteristics of the composition. Although not limited to this category, general examples include additional anti-sebum ingredients and sunscreens.

Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

The composition according to the invention is intended primarily as a product for topical application to human skin, especially as an agent to improve the appearance of aged or photoaged skin.

In use, a quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging

The cosmetic skin composition of the invention can be in any form, e.g. formulated as a toner, gel, lotion, a fluid cream, or a cream. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,057, incorporated by reference herein.

The following specific examples further illustrate the invention, but the invention is not limited thereto.

| List of suppliers | |
|---|---|
| Active Ingredient | Supplier |
| Dextran | Sigma, Dextran Products Corp. |
| Maltodextrin | Grain Processinf Corp. |
| Arabinogalactan | Larex, Inc. |
| Glycolic acid | DuPont |
| Lactic acid | Purac America, Inc. |
| Succinic acid | Sigma |
| Hydrocortisone (water soluble) | Sigma |

EXAMPLE 1

This example measured sting caused by formulations containing glycolic acid.

Procedure for in-vivo sting test: This was a randomized, double blind study where each subject evaluated one test formulation and a control formulation or two test formulations on contralateral nasolabial folds. During the qualification phase, each subject evaluated an 8% glycolic acid test versus a vehicle control (0% glycolic). Subjects with established left/right balanced sensitivity to glycolic acid were qualified. A maximum of 20 qualified subjects (minimum of 15) were utilized in each subsequent test. One paired comparison was made on each testing day, with a minimum of 3 days between sting testing throughout the study. Subjects underwent a 15 second Ivory soap wash regime immediately prior to product testing for enhancing sting response. Any subjects experiencing any stinging/burning on the test sites immediately prior to product application did not have products applied. Study personnel then applied one test formulation and one control or test formulation simultaneously to the appropriate left/right test site, and gently but thoroughly rubbed in. Subjects compared the stinging potential of the two formulations, over a 7.5 minute period using a self-assessment questionnaire.

Sting/Burn Propensity: The degree of stinging/burning felt on the left and right inner cheek and crease of the nose was evaluated using the following scale at the times indicated in Tables below:

0-no stinging/burning; 1-very slight stinging/burning; 2-slight stinging/burning; 3-moderate stinging/burning; 4-moderately high stinging/burning; 5-high stinging/burning; 6-extreme stinging/burning.

Determination of Statistical Significance: At each evaluation time point after baseline, the parametric *paired t-test* (two-tailed) was performed, to compare the extent of attribute change from baseline between each treatment comprising a paired comparison test, with subject acting as a block in these analyses. (Ref. *Statistical Methods*, Snedecor and Cochran, Iowa State University Press, 7th Edition, 1980, pp. 84–86]). The test can be implemented using the SAS software procedure MEANS with the T and PRT options specified.

Forced choice for stinging/burning: At each evaluation point (0,2.5,5.0 and 7.5 min), the response to the forced choice assessment "Which side of the face has more stinging?" was analysed as follows: the number of subjects choosing treatment A was compared to the number of subjects choosing treatment B using a parametric paired t-test (2-tailed). Statistical significance was determined at $p \leq 0.1$. Results from several paired comparisons using this assessment method are shown (see later) in Tables 1B, 2B, 3B and 4B.

An oil-in-water emulsion cream (Base Formula A) was prepared:

| FULL CHEMICAL NAME OR CTFA NAME | % ACTIVE LEVEL IN FORMULATION | TRADE NAME AND % ACTIVE AS RECEIVED |
|---|---|---|
| water, DI | 46.54 | |
| disodium EDTA | 0.05 | Sequesterene Na2 |
| magnesium aluminum silicate | 0.6 | Veegum Ultra |
| methyl paraben | 0.15 | Methyl Paraben |
| simethicone | 0.01 | DC Antifoam Emulsion |
| butylene glycol 1,3 | 3.0 | Butylene Glycol 1,3 |
| hydroxyethylcellulose | 0.5 | Natrosol 250HHR |
| glycerine, USP | 2.0 | Glycerine USP |
| xanthan gum | 0.2 | Keltrol 1000 |
| triethanolamine | 1.2 | Triethanolamine 99% |
| stearic acid | 3.0 | Pristerene 4911 |
| propyl paraben NF | 0.1 | Propylparaben NF |
| glyceryl hydrostearate | 1.5 | Naturechem GMHS |
| stearyl alcohol | 1.5 | Lanette 18DEO |
| isostearyl palmitate | 6.0 | Protachem ISP |
| C12-15 alcohols octanoate | 3.0 | Hetester FAO |

-continued

| FULL CHEMICAL NAME OR CTFA NAME | % ACTIVE LEVEL IN FORMULATION | TRADE NAME AND % ACTIVE AS RECEIVED |
|---|---|---|
| dimethicone | 1.0 | Silicone Fluid 200 (50 cts) |
| cholesterol NF | 0.5 | Cholesterol NF |
| sorbitan stearate | 1.0 | Sorbitan Stearate |
| butylated hydroxytoluene | 0.05 | Embanox BHT |
| tocopheryl acetate | 0.1 | Vitamine E Acetate |
| PEG-100 stearate | 2.0 | MYRJ 59 |
| sodium stearoyl lactylate | 0.5 | Pationic SSL |
| water, DI | q.s. to 99.80 | |

*Unless otherwise noted, active levels were approximately 100%.

The sting/burn of Base Formula A with or without 8% glycolic acid was tested using the in-vivo sting test. The results that were obtained are summarized in Tables 1A and 1B:

TABLE 1A

Sting/Burn Propensity

| Mean Degree of Stinging/Burning (0–6 Scale) | Base Formula A (pH 7.2) | Base Formula A +8% Glycolic Acid (pH 3.8) |
|---|---|---|
| Immediately after application | 0.05 | 1.05 * |
| 2.5 minutes after Application | 0.25 | 1.85 * |
| 5.0 minutes after Application | 0.25 | 2.00 * |
| 7.5 minutes after Application | 0.35 | 2.15 * |

* $p < 0.05$

TABLE 1B

Forced Choice for Stinging/Burning: Which side is worse? Results 7.5 minutes after application

| | Base Formula A (pH 7.2) | Base +8% Glycolic Acid (pH 3.8) |
|---|---|---|
| Number of Subjects Indicating more Discomfort (sting/burn) | 0 | 20 |

* $p < 0.05$

The sting/burn propensity of glycolic at 8% and 4% level were compared. The results that were obtained are summarized in Table 1C.

TABLE 1C

Sting/Burn Propensity

| Mean Degree of Stinging/Burning (0–6 Scale) | Base Formula A + 4% Glycolic Acid (pH 3.8) | Base Formula A + 8% Glycolic Acid (pH 3.8) |
|---|---|---|
| Immediately after application | 0.45 | 1.35 * |
| 2.5 minutes after Application | 0.60 | 1.75 * |
| 5.0 minutes after Application | 0.60 | 1.95 * |
| 7.5 minutes after Application | 0.55 | 1.65 * |

* $p < 0.05$

It can be seen from the results in Tables 1A-1C that 8% glycolic acid at pH 3.8 is significantly more stinging than either the base formulation or 4% glycolic acid. Although, sting can be reduced by increasing pH or lowering the active level, such changes in composition significantly affect dermal delivery and, consequently, the efficacy of the active.

EXAMPLE 2

This example measured the effect of Dextran 10KD on glycolic acid sting at pH 3.8 in Base Formula A. The in-vivo sting test and Base Formula A are described in Example 1.

Base Formula A was prepared without the glycolic acid, base, and dextran. The dextran was solubilized in a separate beaker containing glycolic acid+base (ammonium hydroxide) and a small level of water from the formulation (no more than 5% is needed)—thus, the original Base Formula A was originally made with 5% less water. The glycolic acid/dextran solution was then post added to the Base Formula A during the cool down stage (usually at a temperature of about 45° C.). The results that were obtained are summarized in Tables 2A, 2B and 2C.

TABLE 2A

Sting/Burn propensity

| Mean Degree of Stinging/Burning (0–6 Scale) | Base Formula A + 8% Glycolic + 5% Dextran 10 KD (pH 3.8) | Base Formula A + 8% Glycolic (pH 3.8) |
|---|---|---|
| Immediately after application | 0.73 | 1.32 * |
| 2.5 minutes after Application | 0.53 | 1.11 * |
| 5.0 minutes after Application | 0.26 | 0.68 * |
| 7.5 minutes after Application | 0.26 | 0.52 |

* $p < 0.1$

TABLE 2B

Forced Choice for Stinging/Burning; Which side is worse? Results 2.5 minutes after application

| | Base Formula A + 8% Glycolic + 5% Dextran 10 KD (pH 3.8) | Base Formula A + 8% Glycolic (pH 3.8) |
|---|---|---|
| Number of Subjects Indicating more Discomfort (sting/burn) | 5 | 14* |

* $p < 0.1$

TABLE 2C

Sting/Burn propensity

| Mean Degree of Stinging/Burning (0–6 Scale) | Base Formula A + 8% Glycolic + 5% Dextran 10 KD (pH 3.8) | Base Formula A + 4% Glycolic Acid (pH 3.8) |
|---|---|---|
| Immediately after application | 0.28 | 0.11 |
| 2.5 minutes after Application | 1.11 | 0.89 |
| 5.0 minutes after Application | 1.08 | 0.83 |
| 7.5 minutes after Application | 0.94 | 0.72 |

It can be seen from the results in Tables 2A and 2B that Dextran significantlly reduced the stinging/burning propensity of Base Formula A containing 8% glycolic acid. In Table 2C, the difference in the sting response of the two formulations was not statistically significant, leading to the conclusion that Dextran reduced the sting of 8% glycolic acid formulation to that of 4% glycolic acid formulation.

EXAMPLE 3

This example tested the effect of Dextran 10 KD on succinic acid sting at pH 3.8 in Base Formula A. The test procedure and Base Formula A are described in Example 1. The test formulations were prepared as described in Example 2, except that succinic acid was used in place of glycolic acid. The results that were obtained are summarized in Tables 3A and 3B.

TABLE 3A

Sting/Burn propensity

| Mean Degree of Stinging/Burning (0–6 Scale) | Base Formula A + 8% Succinic + 5% Dextran 10K (pH 3.8) | Base Formula A + 8% Succinic (pH 3.8) |
|---|---|---|
| Immediately after application | 0.17 | 0.33 * |
| 2.5 minutes after Application | 0.27 | 0.83 * |
| 5.0 minutes after Application | 0.55 | 0.55 |
| 7.5 minutes after Application | 0.61 | 0.61 |

$p < 0.1$

TABLE 3B

Forced Choice for Stinging/Burning: Which side is worse? Results 2.5 minutes after application

| | Base Formula A + 8% Succinic + 5% Dextran 10 KD (pH 3.8) | Base Formula A + 8% Succinic (pH 3.8) |
|---|---|---|
| Number of Subjects Indicating more Discomfort (sting/burn) | 5 | 14* |

* $p < 0.05$

It can be seen from the results in Tables 3A and 3B that Dextran significantly reduced the stinging/burning propensity of Base Formula A containining 8% succinic acid.

EXAMPLE 4

This example tested the effect of dextran on glycolic acid sting in a lotion. The test is described in Example 1. The oil-in-water lotion (Base Formula B) was prepared having the following formula:

| FULL CHEMICAL NAME OR CTFA NAME | % ACTIVE LEVEL IN FORMULATION | TRADE NAME AND % ACTIVE AS RECEIVED |
|---|---|---|
| Magnesium Aluminum Silicate | 0.550 | Veegum Ultra |
| 1.3 Butylene glycol | 2.4 | butyleneglycol |
| Disodium EDTA | 0.05 | Clewat-N |
| Xanthan Gum | 0.15 | Keltrol |
| Decaglyceryl monolaurate | 2.0 | Nikkol Decaglyn 1-L |
| Glycerin | 8.0 | Maruko RG |
| Triethanolamine | 2.0 | TEA (99%) |
| Methyl Paraben | 0.195 | methyl paraben |
| Propyl paraben | 0.05 | propyl paraben |
| Sodium Isostearoyl Lactylate | 0.1 | Pationic ISL |
| Sodium carboxymethylcellulose | 0.15 | Cellulose gum 9H4XF |
| Ethyl Oleate | 0.6 | Nofable EO-90 |
| Squalane | 2.0 | Nikkol Squalane |
| Glyceryl Tri (2-Ethylhexanoate) | 3.6 | Panaceat 800B |
| Liquid Petrolatum | 5.8 | Carnation Min Oil |
| Stearic Acid | 0.3 | Pristerene 4911 |
| Cetostearyl Alcohol | 0.5 | Conol 30RC |
| Butyl paraben | 0.05 | Butyl paraben |

13

-continued

| FULL CHEMICAL NAME OR CTFA NAME | % ACTIVE LEVEL IN FORMULATION | TRADE NAME AND % ACTIVE AS RECEIVED |
|---|---|---|
| Hydrogenated Soybean phospholipid | 0.075 | Basis LP-20H (20–30%) |
| Cholesterol | 0.05 | cholesterol |
| di-alpha tocopherol linoleate/oleate | 0.05 | Vitamin E linoleate mixture |
| Dibutylhydroxy toluene | 0.05 | BHT |
| Glycolic acid | 2.80 | Glypure 70 (70%) |
| Glycolic acid/ Ammonium hydroxide solution | 5.08 | GA Mixture NL (82.6%) |
| 4-tertbutyl-4-methoxy-dibenzoylmethane | 0.1 | Parsol 1789 |
| Ethylhexyl 4-methoxycinnamate | 0.1 | Parsol MCX |
| Di-(2-octyldodecyl)-N-lauroyl-L-glutamate | 0.2 | Amiter LG-OD |
| 3-methyl-1,3-butanediol | 1.6 | Isopreneglycol |
| Polyacrylamide/C13-14 Isoparrafin/Laureth 7 | 1.0 | Sepigel 305 |
| Glucose cetostearate/ cetostearyl alcohol | 0.5 | Montanov 68 |
| Ammonium Hydroxide to pH 3.8 | 0–2.0 | Ammonium hydroxide |
| Fragrance | 0.098 | Fleur J412225 QUT |
| Deionized Water | to 100% (59.8%) | Deionized water |

*Unless otherwise noted, active levels are approximately 100%.

The emulsion concentrate was made using all ingredients except glycolic/base/dextran and without all the water. In a separate beaker glycolic+base+dextran+about 5% of the total water was combined and mixed until the dextran solubilizes completely. This mixture was then post added to the emulsion. The pH was then adjusted to the correct pH using base, and then the remainder of the water was added to qs. 100%"

The results that were obtained are summarized in Tables 4A and 4B

TABLE 4A

Sting/Burn propensity

| Mean Degree of Stinging/ Burning (0–6 Scale) | Base Lotion B + 8% Glycolic + 5% Dextran 10 KD (pH 3.8) | Base Lotion B + 8% Glycolic (pH 3.8) |
|---|---|---|
| Immediately after application | 0.22 | 0.22 |
| 2.5 minutes after Application | 0.61 | 1.05 |
| 5.0 minutes after Application | 0.83 | 0.83 |
| 7.5 minutes after Application | 0.93 | 0.93 |

|  | Base Lotion B + 8% Glycolic + 5% Dextran 10 KD (pH 3.8) | Base Lotion B + 8% Glycolic (pH 3.8) |
|---|---|---|
| Number of Subjects Indicating more Discomfort (sting/burn) | 6 | 10 |

It can be seen from the results in Tables 4A and 4B that Dextran reduced the stinging/burning propensity of Base Formula B containing 8% glycolic acid.

14

EXAMPLE 5

Additional dextran molecules were tested for their ability to reduce sting. The test procedure and Formula A are described in Example 1. Base Formula C was as follows:

| FULL CHEMICAL NAME OR CTFA NAME | % ACTIVE LEVEL IN FORMULATION |
|---|---|
| Magnesium Aluminum Silicate | 0.3 |
| Disodium EDTA | 0.05 |
| Methyl hydroxybenzoate | 0.15 |
| 1,3- Butyleneglycol | 3.0 |
| Xanthan Gum | 0.2 |
| Hydroxyethyl cellulose | 0.25 |
| Glycerin Concentrated | 2.0 |
| Triethanolamine | 1.2 |
| Sodium Isostearoyl lactate | 0.5 |
| Glyceryl monostearate | 1.5 |
| Sorbitan Monostearate | 1.0 |
| Polyethyleneglycol monostearate (150 EO) | 1.09 |
| Polyethyleneglycol monostearate (40 EO) | 0.910 |
| Stearyl Alcohol | 1.5 |
| Stearic Acid | 2.0 |
| Isostearyl Palmitate | 6.0 |
| Isocetyl Octanoate | 3.0 |
| Methyl Polysiloxane | 1.0 |
| Cholesterol | 0.5 |
| Dibutylhydroxytoluene | 0.05 |
| Propyl Parahydroxybenzoate | 0.1 |
| dl-Tocopheryl Acetate | 0.1 |
| Glycolic acid | 5.7 |
| Potassium Hydroxide | 1.1 |
| Fragrance | 0.09 |
| DI Water | 66.710 |

The results that were obtained are summarized in Tables 5A, 5B, and 5C.

TABLE 5A

Sting/Burn propensity

| Mean Degree of Stinging/ Burning (0–6 Scale) | Base Formula C + 4% Glycolic + 5% Dextran 40 KD (pH 3.8) | Base Formula C + 4% Glycolic (pH 3.8) |
|---|---|---|
| Immediately after application | 0.27 | 0.16 |
| 2.5 minutes after Application | 0.77 | 2.05* |
| 5.0 minutes after Application | 1.11 | 1.94* |
| 7.5 minutes after Application | 0.77 | 1.66* |

*p < 0.1

TABLE 5B

Sting/Burn propensity; Dextran 10K and Dextran 464K

| Mean Degree of Stinging/Burning (0–6 Scale) | Base Formula A + 8% Glycolic + 5% Dextran 464 KD (pH 3.8) | Base Formula A + 8% Glycolic + 5% Dextran 10 KD (pH 3.8) |
|---|---|---|
| Immediately after application | 0.7 | 0.6 |
| 2.5 minutes after Application | 1.05 | 1.1 |
| 5.0 minutes after Application | 0.8 | 0.85 |
| 7.5 minutes after Application | 0.75 | 0.85 |

TABLE 5C

Sting/Burn propensity; Dextran 10 KD and Dextran 40 KD

| Mean Degree of Stinging/Burning (0–6 Scale) | Base Formula A + 8% Glycolic + 5% Dextran 40 KD (pH 3.8) | Base Formula A + 8% Glycolic + 5% Dextran 10 KD (pH 3.8) |
|---|---|---|
| Immediately after application | 0.68 | 0.74 |
| 2.5 minutes after Application | 1.0 | 1.05 |
| 5.0 minutes after Application | 0.95 | 0.74 |
| 7.5 minutes after Application | 0.79 | 0.58 |

It can be seen from the results in Tables 5A, 5B and 5C that dextrans of varying molecular weights reduce sting equally well.

COMPARATIVE EXAMPLE 6

This example tested various compounds for their ability to reduce sting. The test procedure and Base Formula A are described in Example 1. The results that were obtained are summarized in Tables 6A and 6B.

TABLE 6A

Hydrocortisone

| Mean Degree of Stinging/Burning (0–6 Scale) | Base Formula A + 8% Glycolic + 0.1% Hydrocortisone (pH 3.8) | Base Formula A + 8% Glycolic (pH 3.8) |
|---|---|---|
| Immediately after application | 0.94 | 0.76 |
| 2.5 minutes after Application | 0.68 | 0.58 |
| 5.0 minutes after Application | 0.36 | 0.36 |
| 7.5 minutes after Application | 0.21 | 0.21 |

TABLE 6B

Arabinogalactan

| Mean Degree of Stinging/Burning (0–6 Scale) | Base + 8% Glycolic + 5% Arabinogalactan (pH 3.8) | Base + 8% Glycolic Acid (pH 3.8) |
|---|---|---|
| Immediately after application | 0.89 | 0.47 |
| 2.5 minutes after Application | 1.0 | 0.78 |
| 5.0 minutes after Application | 0.89 | 0.63 |
| 7.5 minutes after Application | 0.63 | 0.52 |

The results in Tables 6A and 6B demonstrate that neither hydrocortisone nor arabinogalactan reduced the sting. In fact, addtion of 5% arabinogalactan (Table 6B) slightly enhanced the sting of the anti-aging cream.

EXAMPLE 7

This example tested the effect of dextran on delivery of various active molecules to the skin layers.

Procedure: Dermal delivery of actives was measured by the In-vitro percutaneous absorption (PCA) test. The tests were carried out using dermatomed pig skin and Bronaugh flow-through cells. 3–4 week old female dorsal pig skin, rinsed with water only was obtained from Buckshire Farms. The skins were stored at −70° C. until use. They were thawed at room temperature, shaved gently with a Norelco electric shaver, sliced to 510 $\mu$m thickness using a Padgett Dermatome, punched into 18-mm discs with a cork borer, and mounted in Bronaugh diffusion cells over 37° C., pH 7.1 Hank's balanced salts buffer flowing at 5 ml/min. After 30 min equilibration, transepidermal water loss was determined using a ServoMed EP1 evaporimeter. Skin discs allowing water losses of >5 g/m2 per hr were replaced. The skin discs were dosed with 2 $\mu$L of product containing the nonlabelled active plus an insignificant weight of the active radiolabelled with 3H or 14C at about 30 microCurie/gram product. The dose was delivered via a displaced volume pipet and spread on the 9-mm diameter exposed skin surface with either a latex finger cot stretched over a cotton tip applicator. Contact times were 6 hours, with receptor fluid being sampled at either 1- or 2-hour intervals in scintillation vials. At the end point, the skin surface was rinsed with triplicate ~1-ml aliquots of water, the skin discs were removed from the apparatus, and blotted with ⅓ of tissue paper (Kim Wipe). The upper surface was tape-stripped 9 times with Scotch transparent tape to obtain the stratum corneum, and the epidermis was separated from the dermis with a scalpel. Analysis by liquid scintillation spectrometry included all samples necessary to account for complete balance and recovery of the radiolabelled material, including product retained on the applicator during delivery, the water-rinsed and excess removed on the tissue, tape stripped stratum corneum, epidermis, dermis (counted after NCS digestion), receptor fluid, the empty Bronaugh cells, filter papers, and rinse pipets. Theoretical applied dose was determined by subtracting the material retained on the applicator from the mean measured radioactivity of a minimum of six weighed 2-uL aliquots of the radiolabelled test product. Data were reported as percent-of-dose in tissue fractions. A p -value of $\leq 0.1$ was considered statistically significant.

Dextran effect on delivery was tested for Base Formula A with either glycolic or succinic acid.

The results that were obtained are summarized in Tables 7A and 7B.

TABLE 7A

| Skin Tissue | Base Formula A + 8% glycolic acid; pH = 3.8 | Base Formula A + 8% glycolic acid + 5% Dextran 10 KD; pH = 3.8 |
|---|---|---|
| Stratum Corneum | 4.6 | 6.6 |
| Epidermis + Dermis | 3.8 | 4.4 |
| Receptor Fluid | 7.5 | 5.6 |
| Total | 15.9 | 16.6 |

TABLE 7B

| Skin Tissue | Base Formula A + 8% succinic acid; pH = 3.8 | Base Formula A + 8% succinic acid + 5% Dextran 10 KD; pH = 3.8 |
|---|---|---|
| Stratum Corneum | 2.4 | 2.4 |
| Epidermis + Dermis | 3.4 | 3.2 |
| Receptor Fluid | 0.8 | 0.3 |
| Total | 6.6 | 5.9 |

It can be seen from the results in Tables 7A and 7B that Dextran did not adversely affect the delivery of either glycolic acid or succinic acid to different skin tissue layers. In fact the presence of Dextran led to a directional increase in delivery of glycolic acid (Table 7A).

Thus, the results of Examples 1–5 demonstrate that dextran reduced the sting caused by weak acids. Other known anti-irritants, such as hydrocortisone, as well as another polysaccharide, arabinogalactan, did not reduce the sting caused by weak carboxylic acids (Comprative Example 6). Unlike numerous prior art approaches, the addition of dextran did not adversely affect the delivery of actives to skin layers (Example 7). Examples 8–10 investigate an additional benefit of combining dextran with an acid active: dextran's ability to enhance the anti-aging efficacy of acid actives.

EXAMPLE 8

This Example investigated the effect of dextran on the ability of hydroxy acids to synthesize collagen in skin fibroblasts.

Collagen is a predominant skin protein. It is synthesized by fibroblasts in the dermis. The synthesis of collagen decreases with aging or photodamage. Collagen 1 is first made as a precursor molecule called Pro-collagen 1. Increased production of procollagen 1 is a marker of an increased collagen level in response to a test compound application.

Method: Neonatal human dermal fibroblasts were purchased from Clonetics Corp., San Diego, Calif. All materials for cell culture were purchased from Life Technologies, NY. Cells (between passages 5–10) were seeded at a density of approximately 10,000/well in the inner 48 wells of a 96-well plate in DMEM (Dulbecco's Modified Eagle's Medium), high-glucose, supplemented with 2 mM L-glutamine, 10% fetal bovine serum, and antibiotic and antimycotic solutions. Cells were then grown to confluence for 2 days. At confluence, the medium was removed and cells were washed with serum-free DMEM, and each well dosed with 200 μl of a solution of a test compound in serum-free DMEM. Each dosing was replicated in the total of six wells. Test compounds were used at concentrations indicated in Table 8 below. Control did not contain a test compound. After 24 hours, the solutions were removed and the cells were redosed with 100 μl of the same solutions. After 24 hours, all solutions were removed, aprotinin was added at a concentration of 0.5% and the solutions stored until analysis at 4° C.

For the analysis of procollagen I in the solutions, they were diluted in DMEM (approximately 20 μl sample in 200 μl DMEM). BioRad slot blot apparatus (BioRad Labs, Calif.) was set up as per manufacturer's instructions. Briefly, nitrocellulose membrane and 3 sheets of filter paper were wetted in TRIS buffered saline (TBS, pH 7.3.) and assembled in the apparatus with the filter paper on bottom and membrane on top. 100 ml TBS was added per well and vacuum filtered. 100 μl of the sample solution was loaded per well and gravity filtered. Procollagen from the test solution was bound to the membrane at this point in the procedure. Membrane was removed from the apparatus and placed in blocking solution (5% milk powder in D-PBS) for 1 hour at RT or overnight at 4C on a rotary shaker. The membrane was then incubated for 1.5 hrs at RT or overnight at 4° C. with 1.5 mL Rat Anti-Human Procollagen Amino-Terminal Ab (Chemicon MAB1912) in TBS with 0.1% BSA (ratio of antibody to buffer/BSA was 1:100) in a sealed bag with shaking. The membrane was then removed; washed 3 times for 5 minutes in TBS/0.1% Tween. The membrane was then incubated for 1 hr at RT or O/N at 4° C. in 2 mL of Biotinylated Anti-Rat Peroxidase-Conjugated Ab (Vector Labs)) in TBS with 0.1% BSA (ratio of antibody buffer/BSA was 1:1000) in a sealed bag with shaking. The membrane was washed 3 times for 5 minutes in TBS/0.1% Tween. 3 mL PBS was incubated with 30 μl each of solutions A(avidin) and B biotinylated Horseradish peroxidase) from Vectastain Elite Kit (Vector Labs) for 30 minutes. The membrane was placed in the resulting solution for 30 minutes in a sealed bag with shaking. The membrane was then removed and washed twice for 5 minutes in TBS/0.1% Tween. The membrane was then stained using the following solution: 12.5 mg 3-amino 9-ethyl carbazole (Sigma), 3.125 mL N,N-dimethylformamide (Sigma), 21.5 mL 0.2M Acetate buffer, pH 5.2 and 12.5 μl $H_2O_2$. The membrane was stained until red/brown color developed and the reaction stopped with 2 washes for 10 minutes in tap water. A transparency of the blot was prepared using a color copier. The color copy was scanned using a laser densitometer (Ultroscan XL from Pharmacia KLB). Percent increase was calculated as a ratio of optical density of cells treated with a test compound over control ×100.

The results that were obtained are summarized in Table 8.

TABLE 8

| Treatment | Collagen (% of control) |
| --- | --- |
| 0.001% Dextran 10 KD | 120* |
| 0.1% Dextran 10 KD + 2 mM Glycolic acid | 120* |
| 0.01% Dextran 10 KD + 2 mM Glycolic acid | 120* |
| 0.001% Dextran 10 KD + 2 mM Glycolic acid | 120* |
| 0.001% Arabinogalactan 50–70 KD | 110 |
| 0.1% Arabinogalactan 50–70 KD + 2 mM Glycolic acid | 110 |
| 0.01% Arabinogalactan 50–70 KD + 2 mM Glycolic acid | 110 |
| 0.001% Arabinogalactan 50–70 KD + 2 mM Glycolic acid | 110 |

*$p < 0.05$

The results in Table 8 demonstrate that the combination of dextran and glycolic acid provided a significant increase in procollagen 1 levels whereas the combination of arabinogalactan and glycolic acid did not.

EXAMPLE 9

This example investigated the ability of dextran to induce keratinocyte differentiation potential of lactic acid.

Keratinocytes, the major cell type in the epidermis, undergo a program of differentiation leading to formation of corneocytes which form the stratum corneum and provide a protective barrier against water loss and entry of harmful substances and pathogens. A prominent feature of keratinocyte differentiation is the formation of a highly insoluble, cross-linked envelope (CE) immediately beneath the keratinocyte plasma membrane. The production of keratinocyte CE is catalyzed by the enzyme transglutaminase-K (Tgase K) which cross-links certain precursor proteins in the cell. Retinoic acid, an agent that is highly effective for improving the appearance of photoaged skin (Weiss etal JAMA, 259:527,1988), has been reported to increase Transglutaminase—K (also referred to as Tgase I) in skin. Therefore, agents that increase Tgase-K activity have the potential of providing benefits to the skin.

Method: Normal Human keratinocytes were seeded in 96-well plates at 4000 cells/well and grown in Keratinocyte Growth Medium (KGM) obtained from Clonetics Corp. Cells were treated with test compounds at various concentrations for 48 hours with an intermittent change of medium after 24 hrs. 6 replicate wells were used for each test. At the end of the incubation period, two parameters were measured on the cells—I. DNA and II. Transglutaminase protein.

I. DNA was measured using a method described by Rago et al Anal. Biochem 191:31–34,1990. Medium was aspirated from the plates, cells were washed 3 times with Phosphate Buffered Saline (PBS). Cells were frozen and thawed 2 times for 5–10 min each. 100 μl of Hoescht Dye (purchased from Calbiochem) solution (1 μg/ml in PBS) was added to each well, plate was covered with foil and let to sit at room temp for 10 min. Readings were then taken on Millipore Fluorescence Miicroplate Reader (ex/em 360/450 nm). Amount of DNA per well (α) was calculated using standards.

II. Dye was removed and the cells were again rinsed 3 times with PBS to prepare for the Transglutaminase (Tgase) assay. 200 μl of 5% Carnation Non-fat milk powder in PBS (blocking solution) was added to each well and left for 1 hr at room temp. This solution was then aspirated, and 100μl of human αTgase 1 monoclonal antibody (Biomedical Technologies) diluted 1/2000 in 1% milk in PBS was added to each well. Plates were incubated for 2 hrs at 37° C. The solutions were then removed and wells washed 4 times with 1% milk/0.05% Tween in PBS. Anti- mouse Fab' conjugated with Horse Radish peroxidase was diluted 1:4000 in 1% milk/0.05%tween/PBS and 100 μl of this solution was added to each well and incubated for 2 hours at 37° C. The solutions were then aspirated, then washed 3 times with 1 % milk/0.05% Tween in PBS. Substrate Solution was prepared by dissolving 2 mg O-Phenylenediamine (Sigma) in 5 mls of citrate buffer and adding 1.65 μl of 30% $H_2O_2$. 100 μl of this substrate solution was added to each well and incubated in the dark for 5 min. The reaction was stopped by adding 50 μl of 4N $H_2SO_4$. Absorbance was measured at 490nm (b). Keratinocyte differentiation was expressed as transglutaminase absorbance (b)/ μg DNA (a).

The results that were obtained in two separate experiments are summarized in Tables 9A and 9B.

TABLE 9A

| Treatment | Percent of Untreated Control |
| --- | --- |
| 2 mM Lactate + 0.1% Dextran 10 KD | 115.3 +/- 99* |
| 2 mM Lactate + 0.01% Dextran 10 KD | 104.3 +/- 7.0 |
| 2 mM Lactate + 0.1% Arabinogalactan 50–70 KD | 99.8 +/- 11.2 |
| 2 mM Lactate + 0.01% Arabinogalactan 50–70 KD | 106.2 +/- 8.5 |
| 2 mM Lactate + 0.1% Dextran 464 KD | 119.2 +/- 8.0* |
| 2 mM Lactate + 0.01% Dextran 464 KD | 126.2 +/- 10.4* |

*p < 0.05

TABLE 9B

| Treatment | Percent of Untreated Control |
| --- | --- |
| 0.1% Dextran 10 KD | 114.1 +/- 5.5* |
| 0.01% Dextran 10 KD | 104.6 +/- 5.6 |

*p < 0.05

The results in Tables 9A and 9B demonstrate that a combination of lactic acid and dextrans (either 10KD or 464KD) significantly increased keratinocyte differentiation whereas the combination with arabinogalactan did not.

EXAMPLE 10

This example investigated the effect of Dextran on the skin anti-aging efficacy of glycolic acid.

Procedure: The study was a 12-week bilateral comparison use test of two formulations.

Subjects were required to come to the laboratory for a prescreen visit to determine if they had a moderate degree of photodamaged skin on both forearms.

Qualified subjects were required to make 6 additional visits over a 12 week period of time. At Baseline (week 0), week 4, 8 and 12, visual evaluation was conducted. Product assignment was randomized and balanced for left/right usage across the subject pool. Subjects were instructed to use the appropriate product to the left/right arms at home and applied approximately 1 gram twice daily for 12 weeks. A minimum of 15 qualified subjects per paired comparison completed the study. Clinical (visual) assessments were conducted for photodamaged (crepe-like/crinkled) skin using the following 10 point scale:

0=none

1–3=mild

4–6=moderate

7–9=severe

The following paired comparisons were made:

Paired comparison 1: base formulation A versus base formulation B+8% glycolic acid.

Paired comparison II: base formulation A+8% glycolic versus base formulation A+8% glycolic+5% Dextran 10 KD.

The Wilcoxon signed rank test, Pratt-Lehmann version, was used to statistically assess the magnitude of average change from baseline attributable to treatment with subject acting as a block in this analysis. In addition, to compare the extent of change from baseline between the two treatments within a cell, the nonparametric Wilcoxon signed-rank test, Pratt-Lehmann version, was also used.

The results that were obtained are summarized in Tables 10A and 10B.

TABLE 10A

Average Improvement in Photodamaged Skin (8% Glycolic versus base)

| Week | 8% glycolic | base |
| --- | --- | --- |
| 0 | 0 | 0 |
| 4 | −0.19 | −0.22 |
| 8 | −0.66* | −0.53 |
| 12 | −1.0 | −0.84 |

*8% glycolic significantly provided significantly greater improvement over base (p < 0.05)

TABLE 10B

Average Improvement in Photodamaged Skin (8% Glycolic versus 8% glycolic + 5% Dextran 10 KD)

| Week | 8% glycolic | 8% glycolic + 5% Dextran 10 KD |
| --- | --- | --- |
| 0 | 0 | 0 |
| 4 | −0.25 | −0.25 |
| 8 | −0.59 | 0.75* |
| 12 | −1.0 | −1.0 |

*8% glycolic + 5% Dextran provided significantly greater improvement over 8% glycolic (p = 0.059).

EXAMPLE 11

This example measured the effect of maltodextrin (Maltrin® 180) on glycolic acid sting at pH 3.8 in Base Formula A. The in vivo sting test and Base Formula A are described in Example 1

TABLE 11A

Sting/Burn Propensity

| Mean Degree of Stinging/Burning (0–6 Scale) | Base Formula A + 8% Glycolic + 5% Maltrin 180 (pH 3.8) | Base Formula A + 8% Glycolic (pH 3.8) |
|---|---|---|
| Immediately after application | 0.69 | 1.00 |
| 2.5 minutes after application | 1.06 | 1.44 |
| 5.0 minutes after application | 0.69 | 1.31* |
| 7.5 minutes after application | 0.44 | 1.13* |

*$p < 0.1$

TABLE 11B

Forced Choice for Stinging/Burning; Which side is worse? Results immediately, 2.5, 5.0, and 7.5 minutes after application

| | Base Formula A + 8% Glycolic + 5% Maltrin 180 (pH 3.8) [number of subjects indicating more sting/burn] | Base Formula A + 8% Glycolic (pH 3.8) [number of subjects indicating more sting/burn] |
|---|---|---|
| Immediately after application | 5 | 11 |
| 2.5 minutes after application | 4 | 12* |
| 5.0 minutes after application | 3 | 13* |
| 7.5 minutes after application | 2 | 14* |

$p < 0.1$

TABLE 11C

Sting/Burn Propensity

| Mean Degree of Stinging/Burning (0–6 Scale) | Base Formula A + 8% Glycolic + 5% Maltrin 180 (pH 3.8) | Base Formula A + 4% Glycolic (pH 3.8) |
|---|---|---|
| Immediately after application | 0.69 | 0.63 |
| 2.5 minutes after application | 0.75 | 0.94 |
| 5.0 minutes after application | 0.44 | 0.75 |
| 7.5 minutes after application | 0.25 | 0.81* |

$p < 0.1$

It can be seen from the results in Tables 11A and 11B that maltodextrin significantly reduced the stinging/burning propensity of Base Formula A containing 8% glycolic acid. The results in Table 11C show that the formulation containing maltodextrin was less stinging than Base Formula A

EXAMPLE 12

Example 12 illustrates topical compositions according to the present invention. The compositions can be processed in conventional manner. They are suitable for cosmetic use. In particular the compositions are suitable for application to aged and/or UV-damaged skin to improve the appearance and the feel thereof as well as for application to healthy skin to prevent or retard deterioration thereof.

A typical oil-in-water emulsion within the scope of the invention is as follows:

| chemical name | wt. % |
|---|---|
| Dextran 10 KD | 4 |
| glycolic acid | 7 |
| propylene glycol | 1 |
| glycerin | 1 |
| hydroxyethylcellulose | 0.5 |
| magnesium aluminum silicate | 0.5 |
| imidazolidinyl urea | 0.5 |
| tetrasodium EDTA | 0.05 |
| petrolatum | 2 |
| isopropyl palmitate | 5 |
| dimethicone | 0.5 |
| cholesterol | 0.5 |
| cetyl alcohol | 0.5 |
| isostearic acid | 3 |
| peg-40 stearate | 1 |
| peg-100 stearate | 1 |
| sorbitan stearate | 1 |
| ammonium hydroxide | to pH 4.0 |
| water DI | qs to 100% |

Another typical oil-in-water emulsion within the scope of the invention is as follows:

| chemical name | wt. % |
|---|---|
| maltodextrin | 5 |
| glycolic acid | 10 |
| propylene glycol | 1 |
| hydroxyethylcellulose | 0.5 |
| magnesium aluminum silicate | 0.5 |
| imidazolidinyl urea | 0.2 |
| petrolatum | 2 |
| isopropyl palmitate | 5 |
| dimethicone | 0.5 |
| cholesterol | 0.5 |
| stearic acid | 3 |
| isostearic acid | 1.5 |
| glycerol stearate | 1.5 |
| peg-40 stearate | 1 |
| peg-100 stearate | 1 |
| sorbitan stearate | 1 |
| cetyl alcohol | 0.5 |
| ammonium hydroxide | to pH 3.8 |
| water DI | qs to 100% |

A typical water-in-oil dispersion within the scope of the invention is as follows:

| chemical name | wt. % |
|---|---|
| isostearyl neopentancate | 20 |
| peg-8 caprylic/capric glycerides | 6 |
| cetyl octanoate | 17 |
| polyglyceryl-6 dioleate | 5 |
| cyclomethicone | 20 |
| glyceryl isostearate | 0.5 |
| isostearic acid | 0.5 |
| ceramide III | 0.1 |
| ppg-5-cetheth-20 | 3 |
| L-lactic acid/potassium lactate | 6 |
| hydroxycaprylic acid | 0.1 |
| water DI | 1.3 |
| Dextran 100 KD | 10 |

The following oil-in-water emulsion within the scope of the invention is prepared:

| chemical name | wt. % |
| --- | --- |
| xanthan gum | 0.2 |
| disodium EDT | 0.1 |
| sodium PCA | 0.5 |
| diazodinyl urea | 0.3 |
| titanium dioxide | 1 |
| stearic acid | 3 |
| cyclomethicone | 0.3 |
| cetyl alcohol | 0.5 |
| glyceryl stearate | 0.5 |
| peg-100 stearate | 0.5 |
| steareth-2 | 0.2 |
| lecithin | 0.5 |
| tocopherol | 0.2 |
| octyl methoxycinnamate | 6 |
| dextran 10K | 6 |
| glycolic acid | 3 |
| malic acid | 2 |
| lactic acid | 2 |
| triethanolamine | to pH 3.8 |
| water DI | qs to 100% |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin cosmetic oil-in-water emulsion composition consisting essentially of:
   (i) from about 0.5 to about 20 wt. % of a dextran or maltodextrin;
   (ii) from 2 to about 12 wt. % of a weak carboxylic acid having pKa of above about 3; and
   (iii) a cosmetically acceptable vehicle; wherein the pH of said composition is in the range of about 3 to about 6.

2. A method of stimulating collagen synthesis by fibroblasts in the skin, the method comprising applying to the skin the composition of claim 1.

3. A method of increasing keratinocyte differentiation, the method comprising applying to the skin the composition of claim 1.

4. A method of treating aged, photoaged, dry, lined or wrinkled skin, the method comprising applying to the skin the composition of claim 1.

5. A skin cosmetic composition consiting essentially of:
   (i) from about 0.5 to about 20 wt. % of a dextran or maltodextrin;
   (ii) from 4 to about 20 wt. % of a weak carboxylic acid having pKa of above about 2 selected from the group consisting of glycolic acid and lactic acid; and
   (iii) a cosmetically acceptable vehicle; wherein said composition is an oil-in-water emulsion; and wherein the pH of said composition is in the range of about 3 to about.

6. The composition according to claim 5 wherein the acid is present in an amount from 4 to 15% by weight.

7. The composition according to claim 5 wherein the acid is present in salt form.

8. The composition according to claim 7 wherein the salt is selected from the group consisting of ammonium, potassium and sodium salts.

9. A skin cosmetic composition consisting essentially of:
   (a) about 0.5 to about 20 wt. % of a dextran or maltodextrin;
   (b) from 4 to about 20 wt. % of glycolic acid; and
   (c) a cosmetically acceptable vehicle;
   wherein said composition is an oil-in-water emulsion; and
   wherein the pH of said composition is in the range of about 3 to about 6.

10. The composition according to claim 9 wherein said glycolic acid is present in salt form.

* * * * *